United States Patent [19]

Aberg et al.

[11] Patent Number: 5,212,165
[45] Date of Patent: May 18, 1993

[54] METHOD FOR REHABILITATING THE VASORELAXANT ACTION OF THE CORONARY ARTERIES IMPAIRED THROUGH ATHEROSCLEROSIS OR HYPERCHOLESTEROLEMIA EMPLOYING AN ACE INHIBITOR

[75] Inventors: A. K. Gunnar Aberg, Lawrenceville; Miguel A. Ondetti, Princeton, both of N.J.

[73] Assignee: E. R. Squibb & Sons, Inc., Princeton, N.J.

[21] Appl. No.: 426,138

[22] Filed: Oct. 23, 1989

[51] Int. Cl.$^5$ .................. A61K 37/00; A61K 31/66; A61K 31/40
[52] U.S. Cl. .................................. 514/114; 514/19; 514/423
[58] Field of Search .................... 514/423, 19, 114

[56] References Cited

U.S. PATENT DOCUMENTS

| | | | |
|---|---|---|---|
| 4,046,889 | 9/1977 | Ondetti et al. | 424/244 |
| 4,316,906 | 2/1982 | Ondetti et al. | 424/274 |
| 4,337,201 | 6/1982 | Petrillo | 548/413 |
| 4,374,829 | 2/1983 | Harris et al. | 424/177 |
| 4,452,790 | 6/1984 | Karanewsky et al. | 424/200 |

FOREIGN PATENT DOCUMENTS 0219782  4/1987  European Pat. Off. .

OTHER PUBLICATIONS

Andrews, P., et al, "Reversal of Experimental Acute Cerebral Vasospasm by Angiotensin Converting Enzyme Inhibition", Stroke, vol. 13, No. 4, Jul.-Aug. 1982, pp. 480-483.

Gavras, H., et al, "Reversal of experimental delayed cerebral vasospasm by angiotensin-converting enzyme inhibition", J. Neurosurg. 5:884-888, (1981).

Miyazaki, S., et al, "Relief from digital vasospasm by treatment with captopril and its complete inhibition by serine proteinase inhibitors in Raynaud's phenomenon," Brit. Med. J., vol. 284, 30 Jan. (1982).

Trubestein, G., et al, "Treatment of Raynaud's phenomenon with captopril", DMW 1984, 109 Jg., Nov. 22, pp. 857-860.

Rustin, M., et al, "The effect of captopril on cutaneous blood flow in patients with primary Raynaud's phenomenon", Brit. J. of Dermatology (1987) 117, pp. 751-758.

Tosi, S., et al, "Treatment of Raynaud's Phenomenon with Captopril", Drugs Exptl. Clin. Res. XIII(1) 37-42 (1987).

Rustin, M., et al, "Chronic leg ulceration with livedoid vasculitis, and response to oral ketanserin", Brit. J. of Dermatology (1989) 120, 101-105.

Coffman, J., "Symptomatic Therapy for Raynaud's Phenomenon", Drug Therapy/Jun. 1989, pp. 95-104.

Madsen, J., et al, "Raynaud's sygdom behandlet med kaptopril (Capoten)", Ugeskr Laeger 146;2695-2697 (1984).

Hartich, L. P., et al, "Effects of antihypertensive agents on vascular responses," Kidney Int. 35:326, (1989).

Shultz, P., et al, "Effect of oral administration of antihypertensive agents on endothelium dependent and endothelium independent vascular relaxation," J. Am. Coll. Cardiol. 13:83A, (1989).

de Nucci, G., et al, "Effect of captopril on the bradykinin-induced release of prostacyclin from guinea pig lungs and bovine aortic endothelial cells," Br. J. Pharmacol., 95(3), 783-8, Nov. 1988.

(List continued on next page.)

Primary Examiner—Frederick E. Waddell
Assistant Examiner—Kimberly R. Jordan
Attorney, Agent, or Firm—Burton Rodney

[57] ABSTRACT

A method is provided for rehabilitating or restoring the vasorelaxant action of the endothelium impaired by atherosclerosis and/or hypercholesterolemia, thereby preventing arteriospasm in the coronary arteries using an angiotensin converting enzyme inhibitor such as captopril, fosinopril, ceranapril, enalapril or lisinopril, which may be administered by oral or parenteral dosage forms.

19 Claims, 2 Drawing Sheets

OTHER PUBLICATIONS

Schoelkens, B., et al, "Local Inhibition of Angiotensin II Formation and Bradykinin Degradation in Isolated Hearts," Clin. Exp. Hypertens. A (10, No. 6, 1259–70, 1988).

van Gilst, W. H., et al, "The Coronary Vasodilatory Mechanism of SH-Containing Converting Enzyme Inhibitors: Potentiation of Endogenous Nitrate," Circulation (78, No. 4, Pt 2, 221, 1988).

Thuermann, P., et al, "Anti-Ischemic Efficacy of Enalapril in Patients with Coronary Heart Disease. A Randomized Placebo-Controlled Double-blind Study (Ger.)," Klin. Wochenschr (66, Suppl. 13, 87, 1988).

Luscher, T. F., et al, "Antihypertensive Treatment Normalizes Decreased Endothelium-Dependent Relaxations in Salt-Induced Hypertension of the Rat," Circulation (74, No. 4, Pt. 2, 286, 1986).

de Nucci, G., et al, "Pressor Effects of Circulating Endothelin are Limited by its Removal in the Pulmonary Circulation and by the release of Prostacyclin and Endothelium-Derived Relaxing Factor," Proc. Natl. Acad. Sci. U.S.A. (85, No. 24, 9797–800, 1988).

The Merck Manual, Fourteenth Ed., 1982, p. 558.

METHOD FOR REHABILITATING THE VASORELAXANT ACTION OF THE CORONARY ARTERIES IMPAIRED THROUGH ATHEROSCLEROSIS OR HYPERCHOLESTEROLEMIA EMPLOYING AN ACE INHIBITOR

FIELD OF THE INVENTION

The present invention relates to a method for rehabilitating or restoring the vasorelaxant action of the endothelium impaired by atherosclerosis and/or hypercholesterolemia, thereby inhibiting or preventing occurrence of vascular vasospasm, especially in the coronary arteries, using an angiotensin converting enzyme (ACE) inhibitor.

BACKGROUND OF THE INVENTION

One of the endogenous factors that modulate vascular tone is the endothelium-derived relaxing factor (EDRF) that is released from the endothelium in the arteries.

It has been shown that several endogenous agents relax vessels only in the presence of an intact endothelium (Furchgott et al, J. Cardiovas. Pharmacol. 6, 336 (1984)) and that this action is mediated by the release of EDRF from the intact endothelium. Acetylcholine is one of these endogenous agents.

There is reason to believe that the EDRF-mediated relaxation of vascular smooth muscle is impaired by hypercholesterolemia and/or atherosclerosis. Thus, cholesterol feeding has been shown to augment vascular contraction to various agents both in vivo (Kawachi et al, "Selective hypercontraction caused by ergonovine in the canine coronary artery under conditions of induced atherosclerosis," Circulation 69:441-450, 1984, Heistad et al, "Augmented responses to vasoconstrictor stimuli in hypercholesterolemic and atherosclerotic monkeys," Circulation Res. 54:711-718, 1984) and in vitro (Henry, P.D. et al "Supersensitivity of atherosclerotic rabbit aorta to ergonovine mediated by a serotonergic mechanism," J. Clin. Inverst. 66:306-313, 1980). Hypercholesterolemia has been shown to blunt the vasorelaxant effect of acetylcholine in iliac rings from cholesterol-fed monkeys (Freiman, P.C. et al, "Atherosclerosis impairs endothelium-dependent vascular relaxation to acetylcholine and thrombin in primates," Circulation Res. 58:783-789, 1986; Harrison, D.G. et al, "Restoration of endothelium-dependent relaxation by dietary treatment of atherosclerosis," J. Clin. Invest. 80:;808-1811, 1987. Furthermore, coronary vessels of patients with atherosclerosis are more subject to vasospasm, particularly in the areas of stenosis (Maseri, A. et al, "Coronary vasospasm as a possible cause of myocardial infarction, a conclusion derived from the study of preinfarction angina," N. Engl. J. Med. 299:1271-1277, 1978), notwithstanding EDRF. Ischemia will occur as a consequence of vascular vasospasm. The effect is of particular importance in the coronary vascular bed that supplies blood to the myocardium.

It is also known that blood vessels of animals with atherosclerosis do not relax well even if acetylcholine is administered even though the blood vessels relax to other stimuli like calcium antagonists.

Captopril has recently been shown to enhance endothelium dependent relaxation of "normal" rat aortic rings in vitro (Hartich, L.P. et al, "Effects of antihypertensive agents on vascular responses," Kidney Int. 35:326, 1989, Shultz, P. et al, "Effect of oral administration of antihypertensive agents on endothelium dependent and endothelium independent vascular relaxation," J. Am. Coll. Cardiol. 13:83A, 1989).

European Patent Application 0219782 to Scholkens discloses the treatment of atherosclerosis, thrombosis and/or peripheral vascular disease in mammals using an angiotensin converting enzyme (ACE) inhibitor or its physiologically tolerable salts. It further discloses that because ACE is predominantly localized in the luminal plasma membrane of the endothelial cell, ACE inhibitors can interfere in platelet-endothelium interaction. In addition, Scholkens discloses that ACE inhibition potentiates the action of bradykinin (a strong stimulator of prostacyclin release from endothelial cells) by inhibiting its degradation and ACE inhibitors, consequently, have an inhibitory effect on platelet aggregation.

G. de Nucci et al, "Effect of captopril on the bradykinin-induced release of prostacyclin from guinea pig lungs and bovine aortic endothelial cells," Br. J. Pharmacol., 95(3), 783-8, Nov. 1988, discloses that in bovine aortic endothelial cells shown on microcarrier beads, captopril (10 mu.K) did not affect the release of prostacyclin or of endothelium-derived relaxing factor (EDRF) induced by bradykinin. They were also ineffective as releasers of EDRF from bovine aortic endothelial cells. Thus, activation of angiotensin-converting enzyme is not involved.

B. Schoelkens et al, "Local Inhibition of Angiotensin II Formation and Bradykinin Degradation in Isolated Hearts," Clin. Exp. Hypertens. A (10, No. 6, 1259-70, 1988) discloses that the interactions of ramipril (RP) and B-3816 (Hoechst) with angiotensin I (ARG-I), angiotensin II (ARG-II) and bradykinin (BK) were studied in isolated rat hearts. It was concluded that BK is involved in the local cardioprotective actions of RP, possibly via releasing PG12 and EDRF.

W. H. van Gilst et al, "The Coronary Vasodilatory Mechanism of SH-Containing Converting Enzyme Inhibitors: Potentiation of Endogenous Nitrate," Circulation (78, No. 4, Pt. 2, 221, 1988) discloses that the coronary vasodilatory mechanism of an SH-containing converting enzyme inhibitor (captopril) was studied in isolated rat heart. These results support the hypothesis that the SH-group of certain ACE inhibitors potentiates the effect of locally increased BK by synergism with endogenous nitrate (EDRF).

P. Thuermann et al, "Anti-Ischemic Efficacy of Enalapril in Patients with Coronary Heart Disease. A Randomized Placebo-Controlled Double-blind Study (Ger.)," Klin. Wochenschr. (66, Suppl. 13, 87, 1988) discloses that in a randomized, placebo-controlled, double-blind, crossover study, enalapril (EN) was shown to have an anti-ischemic effect in 12 angina patients due not only to a fall in the pre- and after-load but perhaps to dilatation of the coronary vessels resulting from the release of the endothelium-derived relaxing factor following bradykinin accumulation induced by inhibition of kininase II as well.

P. Schultz et al, supra, discloses that in hypertension (HPN) both endothelium dependent (EN-D) as well as independent (EN-I) responses to vascular relaxants are depressed. In rats, the authors investigated whether anti-HPN agents affect EN-D and/or EN-I responses to agonists of vascular relaxation. Oral captopril, enalapril and hydralazine differentially affected vascular relaxations in response to EN-D (ACh) and EN-1 (Na nitroprusside) agonists. Indomethacin did not prevent the effect of ACh while both pyrogallol and Hb did inhibit ACh-induced relaxations. Therepeutic efficacy of anti-HPN agents may be modified by their differential effects on EN-D and EN-I vasodilation.

T. F. Luscher et al,"Antihypertensive Treatment Normalizes Decreased Endothelium-Dependent Relaxations in Salt-Induced Hypertension of the Rat," Circulation (74, No. 4, Pt. 2, 286, 1986) discloses that in isolated aorta from hypertensive rats, endothelium-dependent relaxation induced by ACh, adenosine and thrombin, but not Na nitroprusside, was significantly decreased compared to normotensive rats. Responses were unaffected by indomethacin. P.o. hydralazine+-reserpine+hydrochlorothiazide normalized relaxation responses and prevented the development of hypertension, whereas P.o. enalapril was ineffective.

G. de Nucci et al, "Pressor Effects of Circulating Endothelin are Limited by its Removal in the Pulmonary Circulation and by the release of Prostacyclin and Endothelium-Derived Relaxing Factor," Proc. Natl. Acad. Sci. U.S.A. (85, No. 24, 9797-800, 1988) discloses that in vitro, endothelin (EL) contracted rabbit veins and rat stomach, and did not aggregate rabbit or human platelets or prevent their aggregation. Infusion of EL through guinea pig or rat lungs release PG12 and TXA2. Guinea pig lungs removed the EL without being affected by captopril. EL dilated rat mesenteric veins via endothelium-derived relaxing factor (EDRF) release; at higher doses EL cause vasoconstriction.

Andrews, P. et al, "Reversal of Experimental Acute Cerebral Vasospasm by Angiotensin Converting Enzyme Inhibition", Stroke, Vol. 13, No. 4, July-Aug. 1982, p. 480-483 discloses that the angiotensin converting enzyme inhibitor teprotide (SQ 20,881) was studied for its effect on acute cerebral arteriospasm after subarachnoid hemorrhage as determined angiographically in the dog and was found to be effective. At page 482, it is also indicated that "Moreover, in a parallel series of experiments testing the effect of converting enzyme inhibition on the delayed established cerebral arteriospasm, we found that teprotide could reverse that spasm as well. Our preliminary experience with the injectable form of the converting enzyme inhibitor enalapril, (the diacid MK-422) in four dogs with established delayed cerebral arteriospasm, indicates that this agent is at least as effective as teprotide in restoring arterial width in these animals. (Unpublished data).'

'. . . It remains to be determined whether administration of a converting enzyme inhibitor in humans soon after the diagnosis of a subarachnoid hemorrhage can prevent or reverse cerebral arterial spasm, thus duplicating clinically the effects observed in the experimental animals with these compounds."

Gavras, H. et al, "Reversal of experimental delayed cerebral vasospasm by angiotensin-converting enzyme inhibition", J. Neurosurg. 55:884-888, 1981, demonstrated the partial or total release of delayed cerebral vasospasm of the basilar artery and its branches using the ACE inhibitor teprotide administered by injection.

Miyazaki, S. et al, "Relief from digital vasospasm by treatment with captopril and its complete inhibition by serine proteinase inhibitors in Raynaud's phenomenon," Brit. Med. J., Vol. 284, 30 Jan. 1982, discloses that captopril improved a patient's digital circulation.

Trubestein, G., et al, "Treatment of Raynaud's phenomenon with captopril", DMW 1984, 109 Jg., Nov. 22, p 857-860 disclose that 20 patients with primary or secondary Raynaud's phenomenon, in whom prior therapy had included alpha-receptor blockers and other vasoactive substances, were treated with captopril (Lopirin), with marked subjective improvement in 14 cases.

Rustin, M., et al, "The effect of captopril on cutaneous blood flow in patients with primary Raynaud's phenomenon", Brit. J. of Dermatology (1987) 117, p 751-758 disclose that in a placebo-controlled, double-blind cross-over study in 15 patients with Raynaud's phenomenon, p.o. captopril significantly improved cutaneous blood flow but had no effect on frequency or severity of attacks. However, the authors conclude that "a therapy which increases the cutaneous blood flow in these patients does not necessarily influence the triggering factors provoking vasospasm."

Tosi, S., et al, "Treatment of Raynaud's Phenomenon with Captopril", Drugs Exptl. Clin. Res. XIII(1) 37-42 (1987) disclose that captopril significantly decreased the frequency and the severity of ischemic attacks in patients with Raynaud's disease, but did not affect the attacks in patients with scleroderma.

Rustin, M., et al, "Chronic leg ulceration with livedoid vasculitis, and response to oral ketanserin", Brit. J. of Dermatology (1989) 120, 101-105 discloses that no benefit was observed following treatment of a patient suffering from Raynaud's phenomenon and chronic leg ulceration with captopril.

Coffman, J., "Symptomatic Therapy for Raynaud's Phenomenon", Drug Therapy/June, 1989, p. 95-104, discloses that " . . . captopril does not decrease the incidence or severity of peripheral vasospasm in such patients [that is patients with Raynaud's who have hypertension secondary to scleroderma], despite blood pressure control. Captopril cannot be recommended for the treatment of Raynaud's phenomenon in nonhypertensive patients until controlled studies are performed."

U.S. Pat. Nos. 4,046,889 and 4,105,776 to Ondetti et al disclose proline derivatives, including captopril, which are angiotensin converting enzyme (ACE) inhibitors useful for treating hypertension.

U.S. Pat. No. 4,337,201 to Petrillo discloses phosphinylalkanoyl substituted prolines, including fosinopril, which are ACE inhibitors useful for treating hypertension.

U.S. Pat. No. 4,374,829 discloses carboxyalkyl dipeptide derivatives, including enalapril, which are ACE inhibitors useful for treating hypertension.

U.S. Pat. No. 4,452,790 to Karanewsky et al discloses phosphonate substituted amino or imino acids and salts thereof and covers (S)-1-[6-amino-2-[[hydroxy(4-phenylbutyl)-phosphinyl]-oxy]-1-oxohexyl]-L-proline (SQ 29,852, ceranapril). These compounds are ACE inhibitors useful in treating hypertension.

U.S. Pat. No. 4,316,906 to Ondetti et al discloses ether and thioether mercaptoacyl prolines which are ACE inhibitors useful in treating hypertension. This Ondetti et al patent covers zofenopril.

It has now been found that angiotensin converting enzyme inhibitors are capable of relaxing blood vessels impaired through atherosclerosis and/or hypercholesterolemia by rehabilitating the EDRF system.

DESCRIPTION OF THE INVENTION

In accordance with the present invention, a method is provided for rehabilitating or restoring the vasorelaxant action of the endothelium especially the coronary arteries, impaired through atherosclerosis and/or hypercholesterolemia, thereby preventing the occurrence of vascular vasospasm and possible ischemia, in mammalian species, wherein a therapeutically effective amount of an angiotensin converting enzyme inhibitor is administered systemically, such as orally or parenterally.

The method of the present invention is applicable to rehabilitating or restoring the vasorelaxant action of the endothelium, especially the coronary arteries, regardless of whether the patient is suffering from hypertension and thus is effective on hypertensives and normotensives.

Thus, in addition to the already known antihypertensive effect of ACE inhibitors due to blockade of angiotensin II formation and the EDRF-potentiating effect of the ACE-inhibitor captopril in normal arteries as shown by Hartich et al, supra, and Shultz et al, supra, in accordance with the present invention, ACE inhibitors can normalize the impaired EDRF-mediated relaxation due to hypercholesterolemia or atherosclerosis and prevent ischemia that will occur as a consequence of vascular vasospasm. This effect of ACE inhibitors is of particular relevance in the coronary vascular bed that supplies blood to the myocardium.

The angiotensin converting enzyme inhibitor which may be employed herein preferably includes those containing a mercapto (—S—) moiety such as substituted proline derivatives, such as any of those disclosed in U.S. Pat. No. 4,046,889 to Ondetti et al mentioned above., with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

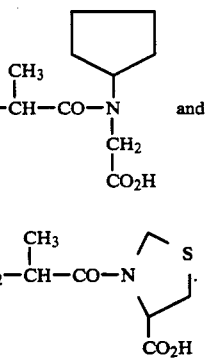

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyl]oxy]-1-oxohexyl]-L-proline (SQ 29,852 or ceranapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]3R(*)]-2-[2-[[1-(ethoxycarbonyl)-3-phenylpropyl]amino[-1-oxo-propyl]-1,2,3,4-tetrahydro-6,7-dimethoxy-3-isoquinoline-carboxylic acid HCl) disclosed in Pharmacologist 26:243, 266 (1984), WY-44221 (Wyeth) disclosed in J. Med. Chem. 26:394 (1983).

Preferred are those ACE inhibitors which are proline or substituted proline derivatives and most preferred are such ACE inhibitors which include a mercapto group.

The above-mentioned U.S. patents are incorporated herein by reference.

In carrying out the method of the present invention, the angiotensin converting enzyme inhibitor may be administered to mammalian species, such as horses, cattle, dogs, cats, and humans, and as such may be incorporated in a conventional systemic dosage form, such as a tablet, capsule, elixir or injectable, as well as suppository dosage forms that release ACE inhibitor in the bloodstream. The above dosage forms will also include the necessary carrier material, excipient, lubricant, buffer, bulking agent (such as mannitol), anti-oxidants (ascorbic acid of sodium bisulfite) or the like. Oral dosage forms are preferred, although parenteral forms such as intramuscular, intraperitoneal, or intravenous enema and suppository forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg.

A preferred oral dosage form, such as tablets or capsules, will contain the ACE inhibitor in an amount of from about 0.1 to about 500 mg, preferably from about 5 to about 200 mg, and more preferably from about 10 to about 150 mg.

For parenteral administration, the ACE inhibitor will be employed in an amount within the range of from about 0.005 mg/kg to about 10 mg/kg and preferably from about 0.01 mg/kg to about 1 mg/kg.

The composition described above may be administered in the dosage forms as described above in single or divided doses of one to four times daily. It may be advisable to start a patient on a low dose and work up gradually to a high dose.

Tablets of various sizes can be prepared, e.g., of about 50 to 700 mg in total weight, containing the active substance in the range described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending the active substance in a conventional liquid vehicle acceptable for pharmaceutical administration so as to provide the desired dosage in one to four teaspoonfuls.

Such dosage forms can be administered to the patient on a regimen of one to four doses per day.

Suppository formulations containing from about 5 to about 250 mg ACE inhibitor may be prepared as well using a conventional suppository base (such as disclosed in U.S. Pat. Nos. 4,344,968, 4,265,875, and 4,542,020) so as provide the desired dosage in one to four suppositories per day.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

The formulations as described above will be administered for a prolonged period, that is, for as long as it is necessary to treat the endothelium disorder and restore the vasorelaxant action of the endothelium. Sustained release forms of such formulations which may provide such amounts biweekly, weekly, monthly and the like may also be employed. A dosing period of at least one to two weeks are required to achieve minimal benefit.

Figure 1:
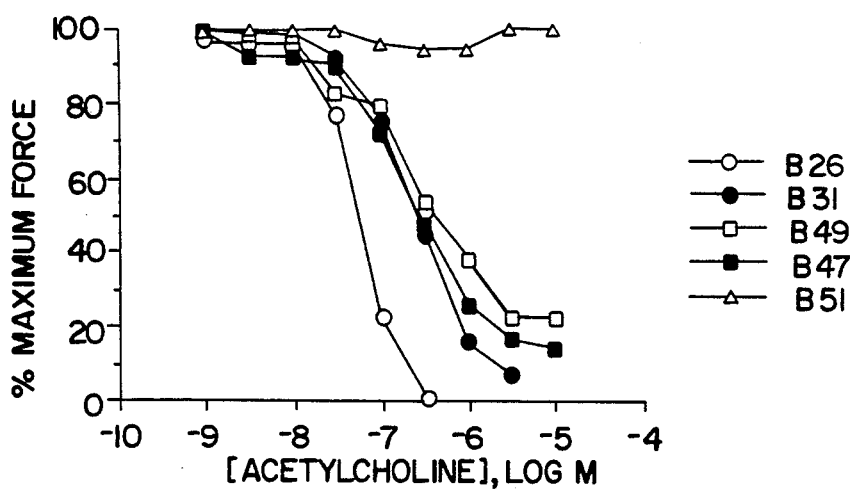
FIG. 1 is a graph showing concentration-response curves to acetylcholine in control monkeys.

All of the above Figures are discussed in Example 20.

The following Examples represent preferred embodiments of the present invention.

EXAMPLE 1

A captopril formulation suitable for oral administration in rehabilitating or restoring the vasorelaxant action of the endothelium, especially the coronary endothelium impaired by atherosclerosis, and thereby prevent the occurrence of coronary vasospasm is set out below.

1000 tablets each containing 100 mg of 1-[(2S)-3-mercapto-2-methylpropionyl]-L-proline were produced from the following ingredients.

| 1-[(2S)-3-Mercapto-2-methylpropionyl]-L-proline (captopril) | 100 g |
|---|---|
| Corn starch | 50 g |
| Gelatin | 7.5 g |
| Avicel (microcrystalline cellulose) | 25 g |
| Magnesium stearate | 2.5 g |

The captopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for restoring the vasorelaxant action of the endothelium impaired by atherosclerosis and/or hypercholesterolemia.

EXAMPLE 2

1000 tablets each containing 200 mg of captopril are produced from the following ingredients:

| Captopril | 200 g |
|---|---|
| Lactose | 100 g |
| Avicel | 150 g |
| Corn starch | 50 g |
| Magnesium stearate | 5 g |

The captopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in rehabilitating or restoring the vasorelaxant action of the endothelium, especially the coronary endothelium impaired by atherosclerosis, and thereby prevent the occurrence of coronary vasospasm.

EXAMPLE 3

Two piece #1 gelatin capsules each containing 250 mg of captopril are filled with a mixture of the following ingredients:

| | |
|---|---|
| Captopril | 250 mg |
| Magnesium stearate | 7 mg |
| USP lactose | 193 mg. |

The resulting capsules are useful in rehabilitating or restoring the vasorelaxant action of the endothelium, especially the coronary endothelium impaired by atherosclerosis, and thereby prevent the occurrence of coronary vasospasm.

EXAMPLE 4

An injectable solution for use in rehabilitating or restoring the vasorelaxant action of the endothelium, especially the coronary endothelium impaired by atherosclerosis, and thereby prevent the occurrence of coronary vasospasm is produced as follows:

| | |
|---|---|
| Captopril | 500 mg |
| Methyl paraben | 5 mg |
| Propyl paraben | 1 mg |
| Sodium chloride | 25 g |
| Water for injection qs. | 5 l. |

The captopril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 100 mg of active ingredient per ml of solution for injection.

EXAMPLE 5

Dosage forms for use in rehabilitating or restoring the vasorelaxant action of the endothelium, especially the coronary endothelium impaired by atherosclerosis, and thereby prevent the occurrence of coronary vasospasm are prepared as described in Examples 1 to 4 except that N-(1-ethoxycarbonyl-3-phenylpropyl)-L-alanyl-L-proline (enalapril) is used in place of captopril.

EXAMPLE 9 AND 10

A suppository formulation containing conventional suppository base such as any of those disclosed in U.S. Pat. Nos. 4,344,968, 4,265,875 or 4,542,020, and N-(1-ethoxy-carbonyl-3-phenylpropyl)-L-alanyl-L-proline (40 mg), (enalapril) or captopril (25 mg), is prepared and is used for rehabilitating or restoring the vasorelaxant action of the endothelium, especially the coronary endothelium impaired by atherosclerosis, and thereby prevent the occurrence of coronary vasospasm.

EXAMPLE 11

A zofenopril formulation suitable for oral administration in rehabilitating or restoring the vasorelaxant action of the endothelium, especially the coronary endothelium impaired by atherosclerosis, and thereby prevent the occurrence of coronary vasospasm is set out below.

1000 tablets each containing 100 mg of zofenopril are produced from the following ingredients.

| | |
|---|---|
| [1(S),4(S)]-1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed gelatin. The with an aqueous solution of the mixture is dried and ground to a fine powder. The Avicel and then the magnesium stearate are admixed with the granulation. This is then compressed in a tablet to form 1000 tablets each containing 100 mg of active ingredient which is used for restoring the vasorelaxant action of the endothelium impaired by atherosclerosis and/or hypercholesterolemia.

EXAMPLE 12

A modified release beadlet formulation capable of slowly releasing the angiotensin converting enzyme inhibitor captopril over a period of up to 6 hours and having the following composition was prepared as described below.

| Ingredient | Amount in Parts by Weight |
|---|---|
| Captopril | 27 |
| Citric acid | 30 |
| Microcrystalline cellulose* | 43 |

*amount may vary to reflect chemical purity of captopril

The above ingredients were mixed and kneaded using water in a planetary mixer to form a wet mass. The wet mass was passed through a Nica E140 extruder to form an extrudate (~1 mm diameter). The extrudate was then passed through a Nica spheronizer to form beadlets. The beadlets were then dried at 40° C. for 12–18 hours in a tray drying oven or for 2–4 hours in a fluid bed dryer. A fraction of the so-formed beadlets were filled into hard shell pharmaceutical capsules for use in rehabilitating or restoring the vasorelaxant action of the endothelium, especially the coronary endothelium impaired by atherosclerosis, and thereby prevent the occurrence of coronary vasospasm.

EXAMPLE 13

A modified release coated-beadlet formulation having the following composition was prepared as follows.

| | | mg/dose |
|---|---|---|
| (i) | Core | |
| | Captopril | 100 mg |
| | Microcrystalline cellulose | 159.1 mg |
| | Citric acid | 37. mg |
| | Lactose | 74.1 mg |
| (ii) | Sealcoat | |
| | Hydroxypropyl methyl cellulose | ca. 8.3 mg |
| | Polyethylene glycol | ca. 2.8 mg |
| (iii) | Barriercoat | |
| | Cellulose acetate phthalate | ca. 4.2 mg |
| | Acetylated monoglycerides | ca. 1.3 mg |

(Myvacet ® 9-40)

The beadlet cores were prepared as described in Example 12. After the dried beadlets were formed, they were coated via a two step process as follows. An aqueous solution of hydroxypropyl methyl cellulose (7.5% by weight) and polyethylene glycol (2.5% by weight) was prepared and sprayed on to the beadlets to form a sealcoat. The beadlets were then coated with a barrier-coat using an aqueous dispersion of cellulose acetate phthalate (30% by weight) mixed with acetylated monoglycerides (9.5% by weight). The beadlets were then filled into hard shell pharmaceutical capsules which are useful in rehabilitating or restoring the vasorelaxant action of the endothelium, especially the coronary endothelium impaired by atherosclerosis, and thereby prevent the occurrence of coronary vasospasm.

EXAMPLE 14

A modified release coated-beadlet formulation having the following composition was prepared as follows.

| Ingredient | % by Weight of Coated Beadlet |
|---|---|
| Core |  |
| Captopril | 26.2 |
| Citric acid | 29.1 |
| Microcrystalline cellulose | 41.8 |
| Film coating |  |
| Hydroxypropylmethyl cellulose phthalate | ca. 2.6 |
| triethyl citrate | ca. 0.3 |

The beadlet cores were prepared as described in Example 12.

Hydroxypropylmethyl cellulose phthalate (9 parts) and triethylcitrate (1 part) were dissolved in ethyl alcohol (90 parts) and then sprayed on to the beadlets to form coated product. The so-formed beadlets were then filled into hard shell pharmaceutical capsules which are useful in rehabilitating or restoring the vasorelaxant action of the endothelium, especially the coronary endothelium impaired by atherosclerosis, and thereby prevent the occurrence of coronary vasospasm.

EXAMPLES 15 TO 19

Following the procedure of Examples 13 to 15 except substituting the following ACE inhibitor, organic acid and binder-excipients, the following beadlet compositions may be prepared which are . useful in rehabilitating or restoring the vasorelaxant action of the endothelium, especially the coronary endothelium impaired by atherosclerosis, and thereby prevent the occurrence of coronary vasospasm.

| Ex. No. | ACE Inhibitor | Organic acid | Binder |
|---|---|---|---|
| 15. | N-(1-ethoxycarbonyl-3-phenyl-propyl)-L-proline | Citric acid | Microcrystalline cellulose |
| 16. | (S)-1-[6-Amino-2-[[hydroxy(4-phenylbutyl)phosphinyl]oxy]-1-oxohexyl]-L-proline | Malic acid | Microcrystalline cellulose and hydroxypropyl methyl cellulose |
| 17. | Lisinopril | Tartaric acid | Na carboxymethyl cellulose |
| 18. | Zofenopril | Succinic acid | Gelatin, pectin and Na carboxymethyl cellulose |
| 19. | Fosinopril | Maleic acid | Microcrystalline cellulose |

EXAMPLE 20

The following experiment was carried out to determine the effect of captopril on the reactivity of iliac arteries from atherosclerotic cynomolgus monkeys.

The experiment was designated to determine whether chronic cholesterol feeding affected the in vitro reactivity of iliac arteries from cynomolgus monkeys and, if so, whether captopril treatment reversed the cholesterol effects.

Twenty-four male cynomolgus (*Macaca fascicularis*) monkeys were divided into four groups of six animals each. During the course of the study, one of the control monkeys was sacrificed due to ill health unrelated to the study. Each group was fed a different diet for six months. The control group ate a normal diet of monkey biscuit. The cholesterol group ate a specially formulated monkey diet containing cholesterol. The cholesterol +low captopril group ate the cholesterol diet supplemented with captopril (50 mg/kg divided into two daily doses). The cholesterol+high captopril group ate the cholesterol diet and a higher total dose of captopril (100 mg/kg divided into two daily doses).

The monkeys were sedated with an intramuscular injection of ketamine (10 mg/kg), then anesthetized with pentobarbital (25 mg/kg). The iliac arteries were carefully dissected, cleaned of surrounding connective tissue, and refrigerated overnight for use the following day. Preliminary experiments indicated that overnight refrigeration did not affect the responses of the tissues to any of the procedures.

On the day of the experiment, three iliac rings (3 mm wide) from each animal were cut and mounted for isometric force recording. Each ring was attached to a micrometer for the control of muscle length and to a Grass FT.03 force transducer and Grass 7D recorder. The rings were placed in warm (37° C.), oxygenated, physiological salt solution (PSS) of the following composition (in mM): 140.0 NaCl, 4.7 KCl, 1.2 $MgSO_4$, 1.6 $CaCl_2$, 1.2 $NaH_2PO_4$, 5.6 D-glucose, 2.0 2-(N-morpholino)propanesulfonic acid (MOPS, pH 7.4 at 37° C.), and 0.02 $Na_2$-ethylenediaminetetraacetic acid (EDTA). The rings were stretched to a preload of 5 g during a 2 hour equilibration period, then stimulated with 1 μM phenylephrine to test for viability and relaxed with 100 nM acetylcholine to test for endothelial function. Stock solutions of phenylphrine, acetylcholine, propranolol, and sodium nitroprusside were prepared daily in water; nifedipine stock solutions were prepared daily in ethanol.

The voltage-dependent calcium channels were studied in one ring from each monkey. The protocol consisted of depleting the cells of calcium by exposing the rings to a Ca-free, EGTA (ethylene glycol-bis($\beta$-aminoethyl ether)N,N,N',N'-tetraacetic acid) PSS (omission of $CaCl_2$ and addition of 0.1 mM EGTA) for 30 minutes. The EGTA was subsequently removed from the tissues with three washes of Ca-free PSS (simple omission of $CaCl_2$). Following that, the rings were bathed in Ca-free, K+PSS (omission of $CaCl_2$ and isoosmotic substitution of KCl for NaCl such that the KCl concentration was 110 mM) for 30 minutes. A $CaCl_2$ concentration-response curve was obtained by replacing the bath solution with K+PSS containing incremental increases in $CaCl_2$ concentration (0.1, 0.3, 0.5, 1.0, 1.25, 1.6, and 2.5 mM). The maximal contractions, in response to 2.5 mM $CaCl_2$, were then relaxed incrementally with nifedipine. Another iliac ring (fade control) from each monkey was subjected to the same protocol with the exception that the strips were allowed to remain contracted and the nifedipine concentration-response curve was not obtained. Some fade of the $CaCl_2$-induced force was observed over the time period required for the nifedipine concentration-response curve. This fade was accounted for by decreasing the amount of relaxation observed upon addition of nifedipine by the amount of fade observed in the time control from the same monkey.

Alpha-adrenoceptor and endothelial cell function were examined in the third ring from each monkey. In the presence of 0.1 $\mu$M propranolol, a cumulative concentration-response curve to phenylephrine was obtained, then the phenylephrine was washed out of the baths and the rings were allowed to relax completely. The rings were subsequently contracted with an $EC_{50}$ concentration of phenylephrine (1 $\mu$M) and, following stabilization of the contraction, the rings were treated with increasing concentrations of acetylcholine, followed by 100 nM sodium nitroprusside.

STATISTICAL METHODS

Data are presented as mean±SEM. The $IC_{50}$ and $EC_{50}$ values were estimated by linearly interpolating from the concentration-response curves. The $EC_{50}$ values for each ring were used to determine the means for each treatment group.

For each monkey, the $EC_{50}$ for acetylcholine relaxation was calculated by linearly interpolating from the concentration-response curves. When 50% relaxation was not achieved, the value of the $EC_{50}$ was set to 30 $\mu$M a value larger than any of the experimental concentrations of acetylcholine). Once these data were obtained, they were transformed by taking ranks of the data.

Linear contrast of mean ranks in the groups were constructed with a variance estimate for the contrast based on the Kruskal-Wallis statistic (Dunn 1964).

In the analyses, the following coefficients were employed: i) for an overall test, the coefficients were 3 for the cholesterol group, 1 for the control group, −1 for the cholesterol+low captopril group, and −3 for the cholesterol+high captopril group, based on prior expectations of likely results; ii) for a test of the cholesterol effect, the coefficients were 1 for the cholesterol group, −1 for the control group, 0 for the cholestrol+-low captopril group, and 0 for the cholesterol+high captopril group; iii) for a test of the captopril effect, the coefficients were 0 for the cholesterol group, 1 for the control group, 0 for the cholesterol+low captopril group, and −1 for the cholesterol+high captopril group.

All statistical results reported are based on one-sided tests. The complete analysis was run with and without the data from the three monkeys whose iliac arteries did not respond to acetylcholine (control B 51, cholesterol B 39, and cholesterol +high captopril B 50).

RESULTS

Contractile Responses to $CaCl_2$

Concentration-response curves to $CaCl_2$ in K+ depolarized rings were obtained following depletion of tissue calcium by repeated washing in Ca-free PSS first with, then without, EGTA. There were no differences in the responses to $CaCl_2$ among any of the treatment groups (Table 1).

TABLE 1

| Group | Responsiveness of K+ depolarized arteries to $CaCl_2$. | |
|---|---|---|
| | Max Force (g) Mean ± SEM | $EC_{50}$ (mM) Mean ± SEM |
| Control | 18.5 ± 1.1 | 0.14 ± 0.01 |
| Cholesterol | 18.2 ± 1.6 | 0.20 ± 0.03 |
| Cholesterol + Low Captopril | 16.5 ± 1.8 | 0.14 ± 0.04 |
| Cholesterol + High Captopril | 16.8 ± 1.1 | 0.15 ± 0.03 |

There were no statistically significant differences between the groups.

Relaxation Responses to Nifedipine

The contractions developed in response to 2.5 mM $CaCl_2$ in K+PSS were relaxed by the cumulative addition of nifedipine. There was no difference in the potency of nifedipine among the various groups of monkeys. The $IC_{50}$ values were (in nM): 11.4±2.3 for control, 22.8±5.6 for cholesterol, 18.8±6.6 for cholesterol+low captopril, and 11.5±1.8 for cholesterol+-high captopril.

In order to control for fade of the $CaCl_2$ contractions, in some rings concentration-response curves were obtained to $CaCl_2$, but not to nifedipine. The force originally developed in response to 2.5 mM $CaCl_2$ was not maintained in these rings. This fade was taken into account in calculating the relaxation associated with nifedipine. The iliac rings from all groups of monkeys faded with approximately the same time course.

Contractile Responses to Phenylephrine

Phenylephrine concentration-response curves were obtained in iliac rings from all groups of monkeys. The data are shown in Table 2.

TABLE 2

| Group | Phenylephrine-induced contractions of isolated iliac arteries. | |
|---|---|---|
| | Max Force (g) Mean ± SEM | $EC_{50}$ ($\mu$M) Mean ± SEM |
| Control | 22.5 ± 1.6 | 0.8 ± 0.1 |
| Cholesterol | 17.3 ± 3.3 | 1.2 ± 0.3 |
| Cholesterol + Low Captopril | 18.4 ± 2.8 | 1.0 ± 0.2 |
| Cholesterol + High Captopril | 19.2 ± 2.2 | 1.3 ± 0.6 |

There were no statistically significant differences between the groups.

Relaxation Responses to Acetylcholine

Iliac rings were contracted with 1 μM phenylephrine and, when force had stabilized, cumulative concentration-response curves were obtained to acetylcholine. The relaxation associated with acetylcholine is dependent upon the presence of a functional endothelium, the ability of EDRF to diffuse to its site of action on the vascular smooth muscle cells, and the responsiveness of the smooth muscle cells to EDRF. The concentration-response curve for each iliac ring is plotted. Some of the rings relaxed only incompletely such that the maximal relaxation was less than 50% of the total possible. For these rings, the $EC_{50}$ value was arbitrarily set at 30 μM for statistical purposes.

Figure 4:
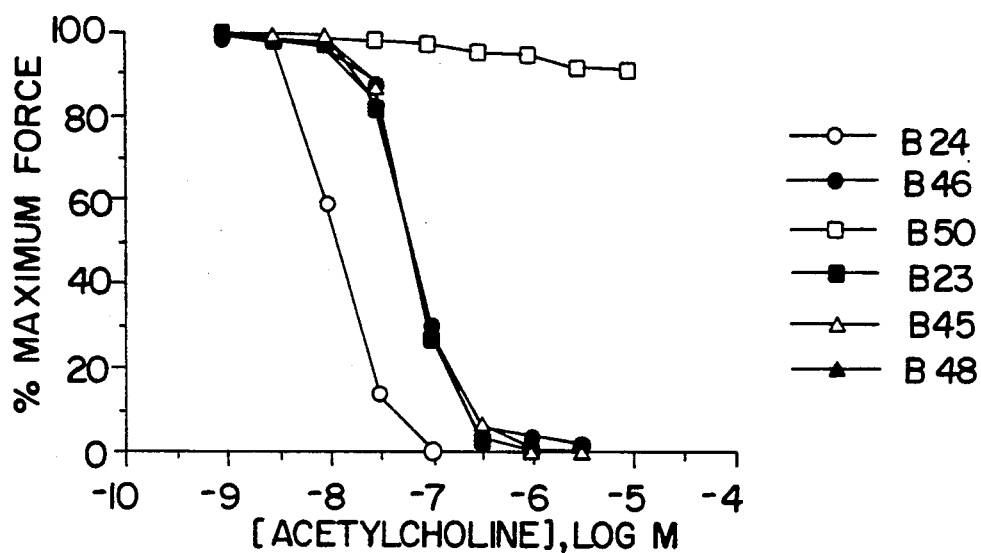
FIG. 4 is a graph showing concentration-response curves to acetylcholine in cholestrol-fed monkeys receiving a high daily dose of captopril (100 mg/kg)

Relaxation was associated with acetylcholine in all but three monkeys: one control monkey (B 51) fed a normal diet (FIG. 1), one monkey (B 39) fed a high cholesterol diet (FIG. 2), and one monkey (B 50) fed a high cholesterol diet and high dose of captopril (FIG. 4). It is believed that the endothelium was damaged in the preparation of those rings for force measurements. Alternatively, it may be speculated that these monkeys had atherosclerotic plaques in their iliac arteries. However, it is believed that the second explanation is less likely because one of the non-responding animals was a control animal that had been fed normal monkey chow (not high in cholesterol). The $EC_{50}$ values for acetylcholine-induced relaxations are shown in Table 3.

TABLE 3

Acetylcholine-induced relaxation of phenylephrine-contracted isolated iliac arteries.

| Group | N | $EC_{50}$ (μM) Mean ± SEM |
|---|---|---|
| Control | 4 | 0.3 ± 0.1 |
| Cholesterol | 5 | 16.2 ± 7.2 |
| Cholesterol + Low Captopril | 6 | 5.1 ± 5.0 |
| Cholesterol + High Captopril | 5 | 0.1 ± 0.01 |

Figure 2:
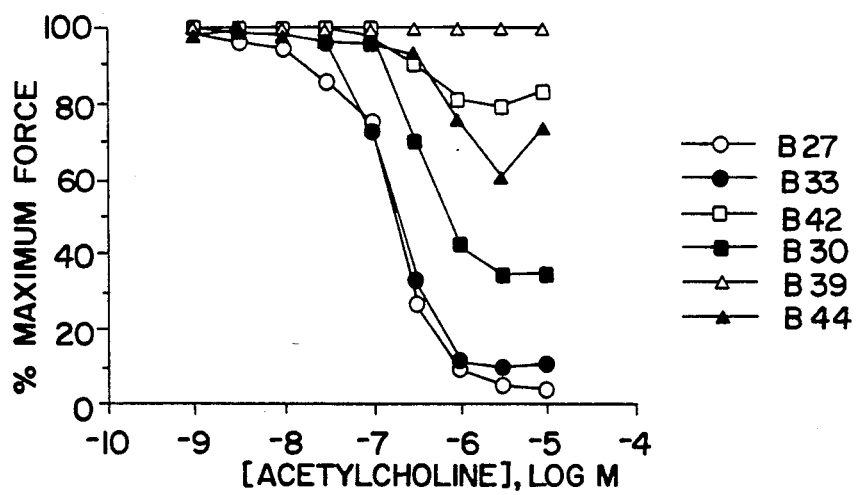
FIG. 2 is a graph showing concentration-response curves to acetylcholine in cholesterol-fed monkeys.

Data from the three non-responding preparations (control B 51, cholesterol B 39, and cholesterol+high captopril B 50) are not included in this table, but are shown in FIGS. 1, 2 and 4. The statistical differences between the groups are shown in Table 4.

A diet high in cholesterol affected the responsiveness of the iliac rings to acetylcholine (FIG. 2). Only two of the iliac rings completely relaxed. One of the iliacs (B 39) did not respond to acetylcholine. Two other rings (B 42 and B 44) did not show 50% relaxation. Also, the concentration-response curves were shifted to the right.

Figure 3:
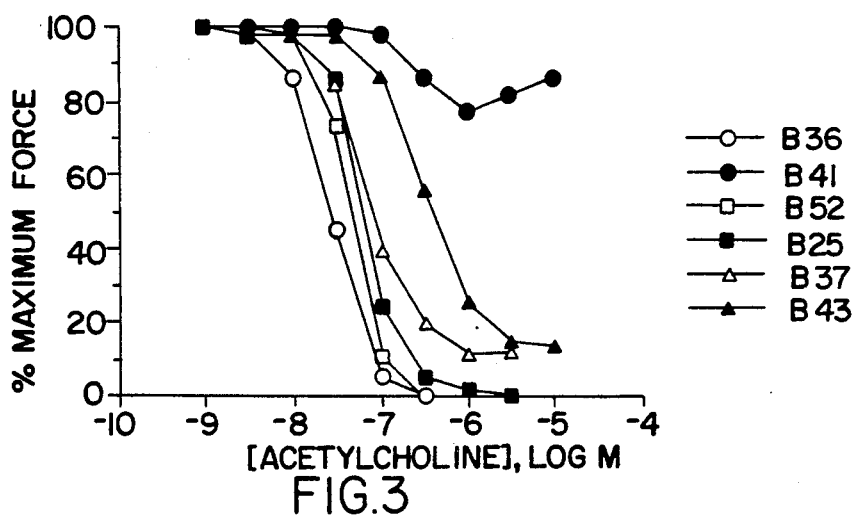
FIG. 3 is a graph showing concentration-response curves to acetylcholine in cholestrol-fed monkeys receiving a low daily dose of captopril (50 mg/kg)

The data curves for acetylcholine-induced responses of iliac rings from monkeys fed a high cholesterol diet and the low dose captopril are shown in FIG. 3. One ring did not show 50% relaxation in response to acetylcholine.

Five of the iliac rings taken from cholesterol fed monkeys that had received the high daily dose of captopril were responsive to acetylcholine. The iliac ring from one monkey in this group was not reactive (FIG. 4).

Figure 5:
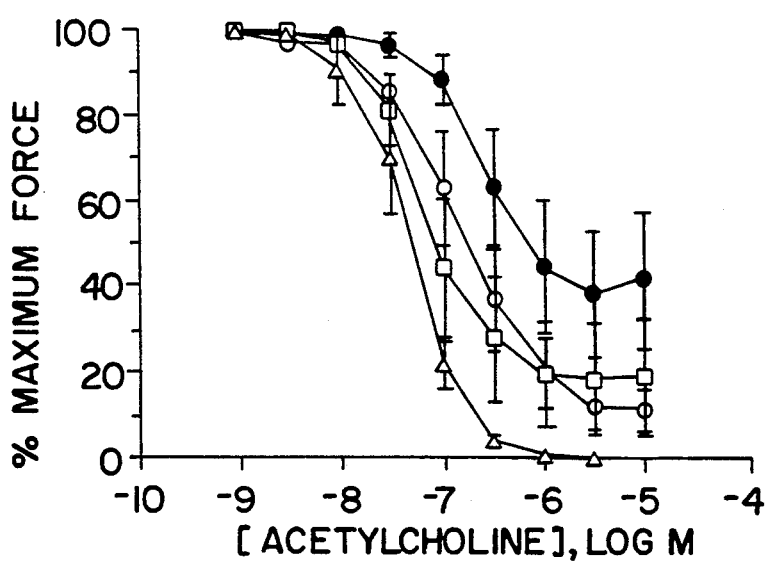
FIG. 5 is a graph showing concentration-response curves to acetylcholine in control (O), cholesterol ( ), cholesterol+low captopril (□), or cholesterol+high captopril (Δ) treated monkeys.

The mean concentration-response curves to acetylcholine are shown in FIG. 5. These curves do not contain the data from the rings which were designated non-responders (control B 51, cholesterol B 39, and cholesterol+high captopril B50). The maximum force generated by each group in response to phenylphrine was (in g): 14.3±1.4 for control, 11.0±2.6 for cholesterol, 12.4±2.2 for cholesterol+low captopril, and 11.9±2.1 for cholesterol+high captopril.

Generally, statistically significant differences were found overall (p<0.01) for the responses of the groups to acetylcholine whether or not the non-responders were included in the analysis (Table 4). Although no significant cholesterol effect was observed, there was a statistically significant effect of captopril as compared with cholesterol (Table 4). For all tests, the statistical results were slightly more significant when the non-responders were eliminated than when they were included in the analyses.

TABLE 4

P-values comparing $EC_{50}$ values for acetylcholine-induced relaxation in the treatment groups.

| Group | Overall | Cholesterol | Captopril |
|---|---|---|---|
| Three non-responders excluded | 0.004 | 0.166 | 0.004 |
| All animals included | 0.008 | 0.200 | 0.013 |

Data were calculated both including and excluding the non-responders.

Relaxation Responses to Nitroprusside

Regardless of how much or how little relaxation was observed in response to acetylcholine, 100 nM nitroprusside caused complete relaxation in every case. This suggests that the defect in the relaxation response was associated with the endothelium or the communication between the endothelium and the smooth muscle cells rather than with the vascular smooth muscle cells themselves.

Discussion

This study compared the in vitro reactivity of iliac arteries from cynomolgus monkeys fed a control diet, a diet high in cholesterol, of a high cholesterol diet plus a low or high dose of captopril. The monkeys were maintained on their diets for six months during which time various determinations were made with regard to their serum cholesterol levels, their blood pressure, etc. At the time of sacrifice, the carotid arteries and aorta were removed, observed for atherosclerotic plaque formation, and prepared for evaluation. At the time of sacrifice the iliac arteries were removed to perform this study on vascular reactivity and EDRF-related relaxations of the tissues.

The $CaCl_2$ concentration-response curves obtained in the four groups of animals were essentially superimposable as were the curves for nifedipine. These findings suggest that the voltage-dependent calcium channels were not affected by cholesterol feeding in the presence or absence of captopril. The responses to phenylephrine were also very similar in the control and cholesterol (with or without captopril) groups indicating that the alpha-adrenoceptors were unaffected. Taken together, these data point to a lack of effect of any of the dietary treatments on excitation-contraction coupling mechanisms in the vascular smooth muscle cells.

Contrary to the findings of Freiman et al, supra, (1986) and of Harrison et al, supra, (1987), there was no statistically significant cholesterol effect on acetylcholine induced relaxation in the present study. It was found, however, that acetylcholine was significantly more potent and efficacious in iliac rings from the cholesterol-fed monkeys which received captopril than in iliac rings from animals fed a cholesterol diet without additional dosing of captopril. Captopril feeding alone (without cholesterol) has previously been shown to potentiate the effects of acetylcholine in rat aortic rings in vitro (Hartich et al, supra, 1989, Shultz et al, supra, 1989).

The lack of response to acetylcholine observed in some rings might have been due to tissue damage caused by handling or by atherosclerotic plaques. The contractile regulatory systems of the vascular smooth muscle cells were intact, because nitroprusside was able to cause complete relaxation of every ring.

The results obtained showed that neither cholesterol nor captopril affected the in vitro responses of the iliac arteries to phenylephrine, $CaCl_2$ or nifedipine. However, there was a statistically significant trend for the $EC_{50}$ concentration of acetylcholine to vary depending on the treatment such that: cholesterol>control>low captopril>high captopril. Although not statistically significant, there was a tendency for the cholesterol treated iliacs to relax less in response to acetylcholine as compared with the control vessels. Captopril significantly shifted the $EC_{50}$ concentration for acetylcholine to the left as compared with cholesterol alone. Thus, captopril was shown to enhance endothelium-dependent vasorelaxant effects in arteries from hypercholesterolemic and atherosclerotic monkeys. This effect of captopril is of therapeutic significance in patients in preventing occurrence of vasospasm, especially in the coronary arteries, and thereby prevent ischemia.

What is claimed is:

1. A method for rehabilitating or restoring the vasorelaxant action of the coronary endothelium impaired through atherosclerosis and/or hypercholesterolemia, in a mammalian specie, to thereby prevent occurrence of coronary vasospasm, which comprises administering to a mammalian specie in need of such treatment a therapeutically effective amount of an angiotensin converting enzyme inhibitor.

2. The method as defined in claim 1 wherein the vasorelaxant action of the coronary arteries is restored to thereby prevent coronary vasospasm.

3. The method as defined in claim 2 wherein the coronary arteries are impaired through atherosclerosis.

4. The method as defined in claim 2 wherein the coronary arteries are impaired through hypercholesterolemia.

5. The method as defined in claim 1 wherein the angiotensin converting enzyme inhibitor is a mercapto containing ACE inhibitor.

6. The method as defined in claim 1 wherein the angiotensin converting enzyme inhibitor is a phosphonate substituted amino or imino acid or salt thereof, a proline derivative, a substituted proline derivative, a mercaptoacyl derivative of a substituted proline, a carboxyalkyl dipeptide derivative, a phosphinylalkanoyl proline derivative or a phosphonamidate derivative.

7. The method as defined in claim 1 wherein said angiotensin converting enzyme inhibitor is a proline derivative or a substituted proline derivative.

8. The method as defined in claim 1 wherein said angiotensin converting enzyme inhibitor is a carboxyalkyl dipeptide derivative.

9. The method as defined in claim 1 wherein said angiotensin converting enzyme inhibitor is a phosphinylalkanoyl proline derivative, a phosphoramidate derivative, or a phosphonate substituted amino or imino acid or salt thereof.

10. The method as defined in claim 1 wherein said angiotensin converting enzyme inhibitor is captopril.

11. The method as defined in claim 1 wherein said angiotensin converting enzyme inhibitor is enalapril.

12. The method as defined in claim 1 wherein said angiotensin converting enzyme inhibitor is lisinopril.

13. The method as defined in claim 1 wherein said angiotensin converting enzyme inhibitor is zofenopril.

14. The method as defined in claim 1 wherein said angiotensin converting enzyme inhibitor is fosinopril.

15. The method as defined in claim 1 wherein said angiotensin converting enzyme inhibitor is (S)-1-[6-amino-2-[[hydroxy(4-phenylbutyl)phosphinyl]oxy]-1-oxohexyl]-L-proline (ceranapril).

16. The method as defined in claim 1 wherein said angiotensin converting enzyme inhibitor is administered in single or divided doses of from about 0.1 to about 500 mg/one to four times daily.

17. The method as defined in claim 1 wherein the angiotensin converting enzyme inhibitor is administered to a hypertensive patient.

18. The method as defined in claim 1 wherein the angiotensin converting enzyme inhibitor is administered to a normotensive patient.

19. A method for rehabilitating or restoring the vasorelaxant action of the coronary endothelium impaired through atherosclerosis and/or hypercholesterolemia, in a normotensive patient, to thereby prevent occurrence of coronary vasospasm, which comprises administering to a normotensive patient in need of such treatment a therapeutically effective amount of an angiotensin converting enzyme inhibitor.

* * * * *